United States Patent [19]

Stowell

[11] Patent Number: 4,885,531

[45] Date of Patent: Dec. 5, 1989

[54] CONTINUOUS DETERMINATION AND CONTROL OF THE WEIGHT OF HAY BALES DURING THE BALING PROCESS

[76] Inventor: Dennis E. Stowell, P.O. Box 796, Parowan, Utah 84761

[21] Appl. No.: 322,353

[22] Filed: Mar. 13, 1989

Related U.S. Application Data

[63] Continuation-in-part of Ser. No. 13,130, Feb. 10, 1987, Pat. No. 4,812,741.

[51] Int. Cl.[4] ............................................. G01N 5/02
[52] U.S. Cl. ....................................... 324/65 P; 73/73
[58] Field of Search ................. 324/65 P, 65 R, 61 R; 73/73; 56/10.2

[56] References Cited

U.S. PATENT DOCUMENTS

| | | | |
|---|---|---|---|
| 2,548,410 | 4/1951 | Tyson | 324/65 P |
| 2,647,394 | 4/1953 | Schaeperklaus | 73/73 |
| 3,360,722 | 12/1967 | Bethmann et al. | 73/73 |
| 3,999,134 | 12/1976 | Lorenzen | 324/61 R |
| 4,170,251 | 10/1979 | Hine, II | 73/73 |
| 4,509,361 | 4/1985 | Johnson | 73/73 |
| 4,750,143 | 6/1988 | Heitz et al. | 324/61 R |
| 4,780,665 | 10/1988 | Mitchell | 324/65 R |
| 4,812,741 | 3/1989 | Stowell | 324/65 P |

Primary Examiner—Reinhard J. Eisenzopf
Assistant Examiner—Maura K. Regan
Attorney, Agent, or Firm—Norman B. Rainer

[57] ABSTRACT

A bale weight control system is provided for use on a conventional baling machine having a compression zone defined by opposed retaining walls capable of being urged together by a hydraulic ram. The weight control system utilizes a moisture sensing system which provides a continuous electrical output signal to a microprocessor that determines proper wall pressure. The microprocessor produces an electrical output signal that controls the hydraulic pressure supplied to the ram. Water may be controllably applied to hay which is too dry.

8 Claims, 3 Drawing Sheets

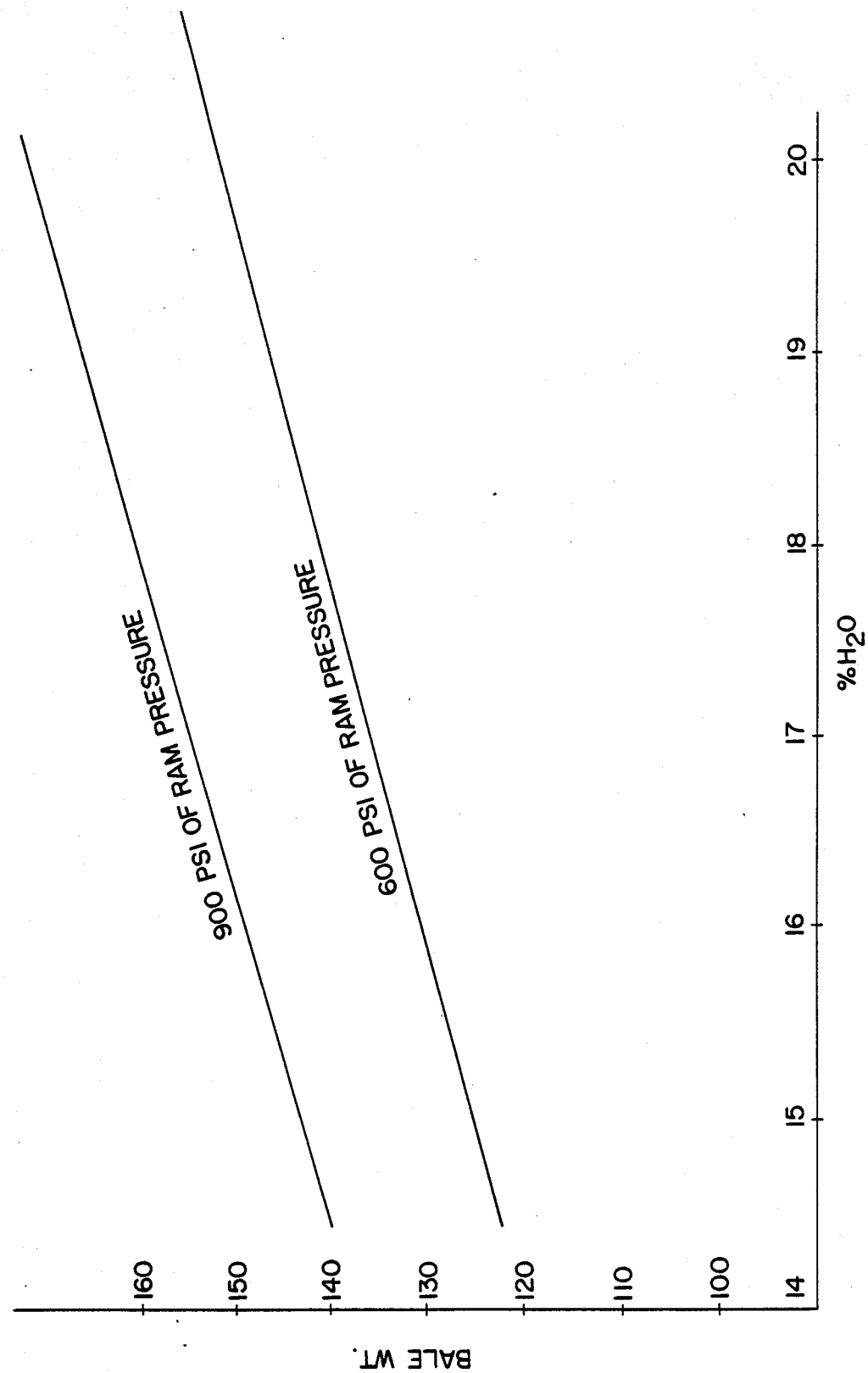

CONTINUOUS DETERMINATION AND CONTROL OF THE WEIGHT OF HAY BALES DURING THE BALING PROCESS

PRIOR APPLICATIONS

This Application is a continuation-in-part of U.S. patent application Ser. No. 013,130, filed 02/10/87 now U.S. Pat. No. 4,812,741.

BACKGROUND OF THE INVENTION

This invention concerns the determination and control of the weight of hay bales during the baling process.

The weight of individual bales of hay during the baling process is a critical variable which affects the marketability of the bales in several ways. These include such factors as freight cost from production site to market location, suitability of the bales for the horse hay market versus the dairy market or other uses, quality of the baled hay, and others. In addition, continuous weighing of bales allows production tonnages to be immediately calculated and made available to management for production inventory purposes.

Individual bale weight can be determined in several ways. For example, each bale can be individually weighed while momentarily stationary as it exits the baler. This method is labor intensive to the point of prohibiting it as a practical expedient. Alternatively, some type of force-detecting device may be attached to the exit chute of the baler to determine the weight of moving bales. Suitable force-detecting devices include strain gauge load cells, spring and hydraulic activated scales, weighted balance beams, and other devices. The latter method, although in use to some degree, suffers from the disadvantages of inaccuracy due to vibration and severe maintenance problems because of the very harsh baler environment.

Conventional hay baler machines are generally comprised of: (a) a driver's compartment, (b) a feeder mechanism which picks the hay up from the ground, (c) a section which distributes the hay to form a relatively uniform stream, (d) a forming chamber wherein the stream is compacted and formed into the desired shape and size, and (e) a squeeze rail region where the shaped stream is further compacted and wrapped with wire or twine to form the finished bale which is discharged onto the ground. The forming chamber and squeeze rail region, which may be generically characterized as compression zones, have flat retaining walls against which the hay slides as it advances through the baler. The hay will generally pass through said compression zones at a linear flow velocity of between about 150 and 500 inches per minute. The flow is substantially continuous, although having in certain instances a uniformly pulsed motion caused by the compacting mechanisms. Finished bale density varies from approximately 8 to 15 pounds per cubic foot.

The dependence of bale weight upon bale moisture content has long been recognized by baler manufactures. For a given hay baler, the higher the moisture of the hay passing through the baler, the heavier the bale will be. This is due to several factors, namely: (a) the additional weight which the moisture adds to the hay; (b) the greater coefficient of friction with respect to the baler walls; and (c) the softer, more compliant nature of the wet hay which makes it more compressible at a given pressure.

The moisture level of a given windrow of hay is often not uniform throughout its length. This is caused by factors such as ground terrain (hay located in swales is usually of higher moisture content than hay located on ridges), ground moisture, quantity of weeds contained in the hay, windrow size, and other factors. Therefore, the weights of bales in a given field will vary as the moisture content varies if no adjustments are made during baling to compensate for fluctuations in the moisture content of the hay being baled.

In order for the baler operator to have control of the weight of bales being produced, the side walls and/or top and bottom walls of the compression chamber are constructed to be adjustable so that the distance of separation between opposed walls can be varied. By virtue of the construction of the baler and its manner of operation, the pressure applied to the hay increases as the distance between opposed walls diminishes, (thus increasing or decreasing the friction force between the hay and the compression chamber walls). The adjustment of the wall spacing results in bales which are more or less dense and which thus weight more or less. In this manner, as the moisture content of hay which is being baled increases, causing the friction coefficient and therefore the bale weight to increase, the baler operator can reduce the wall pressure on the hay and maintain a constant bale weight at a given bale size.

The adjustment of the spacing between the walls is generally controlled through either a hydraulic ram or through a hand adjustable squeeze mechanism. Although the baler operator has control of the bale weight, no satisfactory method of measuring the weight of each bale being produced has been designed.

It is accordingly an object of this invention to provide a bale weight monitoring system which is continuous in nature and which is directly associated with the baler such that every bale which is baled may be immediately checked for bale weight.

It is another object of this invention to provide a method utilizing a system as in the foregoing object which determines bale weight during the baling process so that appropriate adjustments can be made to retain the bale weight within acceptable limits.

It is another object of this invention to provide a method of adding water to a bale in cases where hay being baled is of too low moisture content, and to control the amount of water being added by continuously monitoring the moisture content of the hay.

It is a further object of this invention to provide a method of the aforesaid nature which provides an output signal dependent on the weight of individual bales being formed during the baling process, said signal serving to control the hydraulic ram or rams to provide a uniform bale weight.

It is a still further object of the present invention to provide a system of the aforesaid nature comprised of apparatus components of rugged, durable construction capable of withstanding the corrosive, abrasive conditions prevalent within and about a hay baler.

It is yet another object of the invention to provide apparatus components of the aforesaid nature amenable to low cost manufacture and facile installation into conventional hay baling equipment.

It is a further object of this invention to provide a method of the aforesaid nature which provides an output signal dependent on the moisture content of the hay, said signal serving to control the amount of water added to the bale in cases where the hay is too dry.

These objects and other objects and advantages of the invention will be apparent from the following description.

SUMMARY OF THE INVENTION

The above and other beneficial objects and advantages are accomplished in accordance with the present invention by a bale weight control system for a conventional baling machine having a driver's compartment and a compression zone defined by opposed parallel flat retaining walls capable of being urged together by hydraulic force means, said control system comprising:

(1) a moisture sensing system comprised of a battery-operated conductivity meter installed upon one of said walls and associated analog-to-digital convertor located in said driver's compartment, said conductivity meter having positive and negative input terminals and providing a readout of percent moisture, and an auxllary digital output of the moisture, and associated electrical conductors, said sensing system continuously monitoring the moisture content of hay passing through said compression zone, and an output signal which is related to and dependent upon the moisture content of the hay being baled and which is used to control the amount of water being added to the bale, (2) a hydraulic pressure sensing system consisting of a pressure transducer, an electric meter, and an analog-to-digital converter located in the driver's compartment which continuously monitors the hydraulic pressure of said hydraulic force means, .

(3) a battery-operated microprocessor adapted to combine the signals from said moisture sensing system and hydraulic pressure sensing system to produce a third signal which is related to and dependent upon the weight of a bale being produced at a given point in time, such microprocessor using a definite relationship between moisture content of the hay and hydraulic pressure to determine the bale weight, said relationship being determined by calibration of the system for a given baler configuration, and dependent upon the type of crop being baled and the configuration of the baler upon which the system is being used, (4) electrically controlled valve means responsive to the output signal from the microprocessor to adjust hydraulic pressure and thereby maintain a constant weight to the bales being produced, (5) indicator gauge means located in the driver's compartment for providing to the operator a continuous indication of the weight of bales being produced as well as instantaneous readings of hay moisture content and hydraulic pressure, (6) electrically controlled valve means responsive to the output signal described in 1 above to adjust the quantity of water being added to the bale in cases where the hay being baled is too dry, (7) electrical conductors which interconnect the moisture monitoring system, the hydraulic pressure monitoring system, the hydraulic oil and water control valve means, the microprocessor and the gauge means.

In preferred embodiments, the moisture sensing system will consist of the BALER-MOUNTED CONTINUOUS MOISTURE MONITORING SYSTEM described in U.S. patent application Ser. No. 07/013,130, filed 2/10/87.

BRIEF DESCRIPTION OF THE DRAWING

For a fuller understanding of the nature and objects of the invention, reference should be had to the following detailed description taken in connection with the accompanying drawing forming a part of this specification and in which similar numerals of reference indicate corresponding parts in all the Figures of the drawing:

FIG. 3 is a graph showing the calibration relationship between bale weight, hay moisture content, and ram hydraulic pressure for a Freeman 330 baler operating on first crop alfalfa hay.

DESCRIPTION OF THE PREFERRED EMBODIMENT

Figure 1:
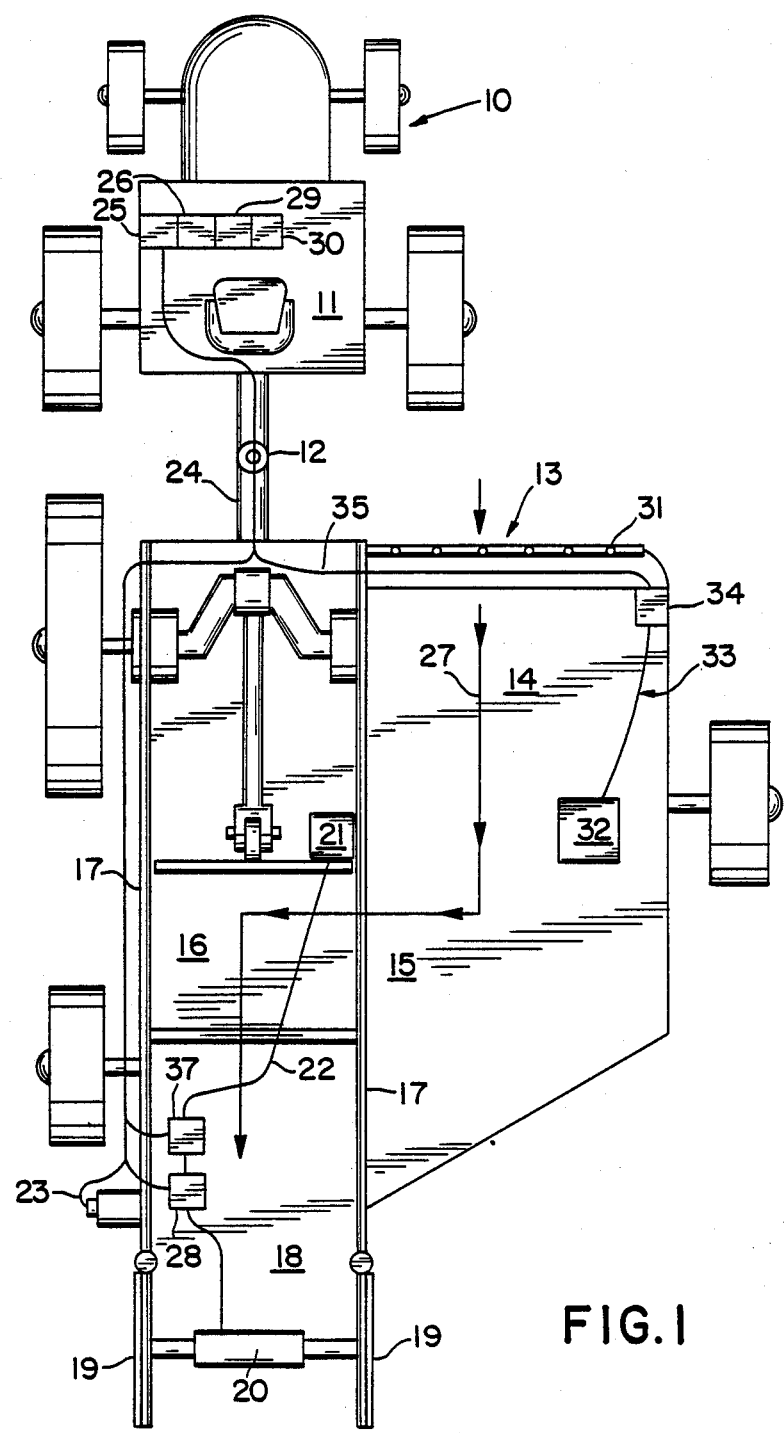
FIG. 1 is a schematic top view of an embodiment of the monitoring system of this invention shown in functional association with a conventional baler/tractor combination.

Referring to FIG. 1, a conventional hay baling machine is shown comprised of tractor 10 having driver's compartment 11 and a rearwardly disposed omni-directional hitching device 12 which joins the tractor to baler unit 13. Said baler unit is comprised of a feeder mechanism 14 which gathers hay and advances it to a distributor zone 15 which delivers the hay to forming chamber 16. Chamber 16, bounded by stationary retaining walls 17, is essentially a first compression zone wherein the hay undergoes initial compaction. The hay is further compacted in squeeze rail section 18 bounded by opposed movable walls 19. A hydraulic ram 20 is interactive between walls 19. The ram 20 is pressurized by pressure pump 21 and communicating hydraulic line 22. The compacted and baled hay emergent from the squeeze rail section is discharged onto the ground behind the baler unit. The arrowed line 27 indicates the general path taken by the hay.

A conductivity meter 23 is positioned within one of walls 17 in a manner such that the moving hay slidingly contacts the meter. The nature of the meter and its exact method of mounting may be as described in U.S. patent application Ser. No. 013,130, filed 2/10/87. The conductivity meter is preferably battery-operated, having positive and negative input terminals, and is connected by insulated conductor wires 24 to an analog-to-digital converter 25 located in the driver's compartment. A gauge 26, associated with converter 25, indicates moisture content of the monitored hay.

A pressure transducer 28 mounted within hydraulic line 22, transmits an appropriate electrical signal through wires 24 to a pressure-indicating gauge 29 in the driver's compartment.

A battery-operated microprocessor 30, positioned adjacent gauges 29 and 26, receives signals from conductivity meter 23 and transducer 28 and enters said signals into a computer analysis which produces an output or control signal. The control signal is routed by wires 24 to valve means 37 which controls the hydraulic pressure admitted to ram 20.

By virtue of said components and their interaction, the moisture level detected by conductivity meter 23 automatically controls the pressure applied upon the hay by movable walls 19. The manner of control of the pressure applied by walls 19 is dictated by the computer analysis to produce bales of constant weight.

The exemplary calibration relationship shown in FIG. 3, which reflects the computer analysis program, was obtained for the specific combination of: a Freeman 330 3-wire baler, a Delmhorst F-4 moisture detector with a baler mounted sensor described in U.S. patent application Ser. No. 013,138, dated 02/10/87, a pressure gauge on the hydraulic ram, and a manual bale weighing scale. Data was accumulated to determine the dependence of bale weight upon the variables of hay moisture content and hydraulic ram pressure.

A means 31 of adding water to the hay prior to baling is positioned above the windrow in front of feeder mechanism 14. Water is supplied to the water adding means 31 by a hose 33 which carries the water from the water storage source 32. The water added may be in the form of either liquid water or as steam. An electrically activated water control valve 34 is located in the water line 33 and is connected to the conductivity meter 23 output signal with an electrical conductor 35.

Figure 2:
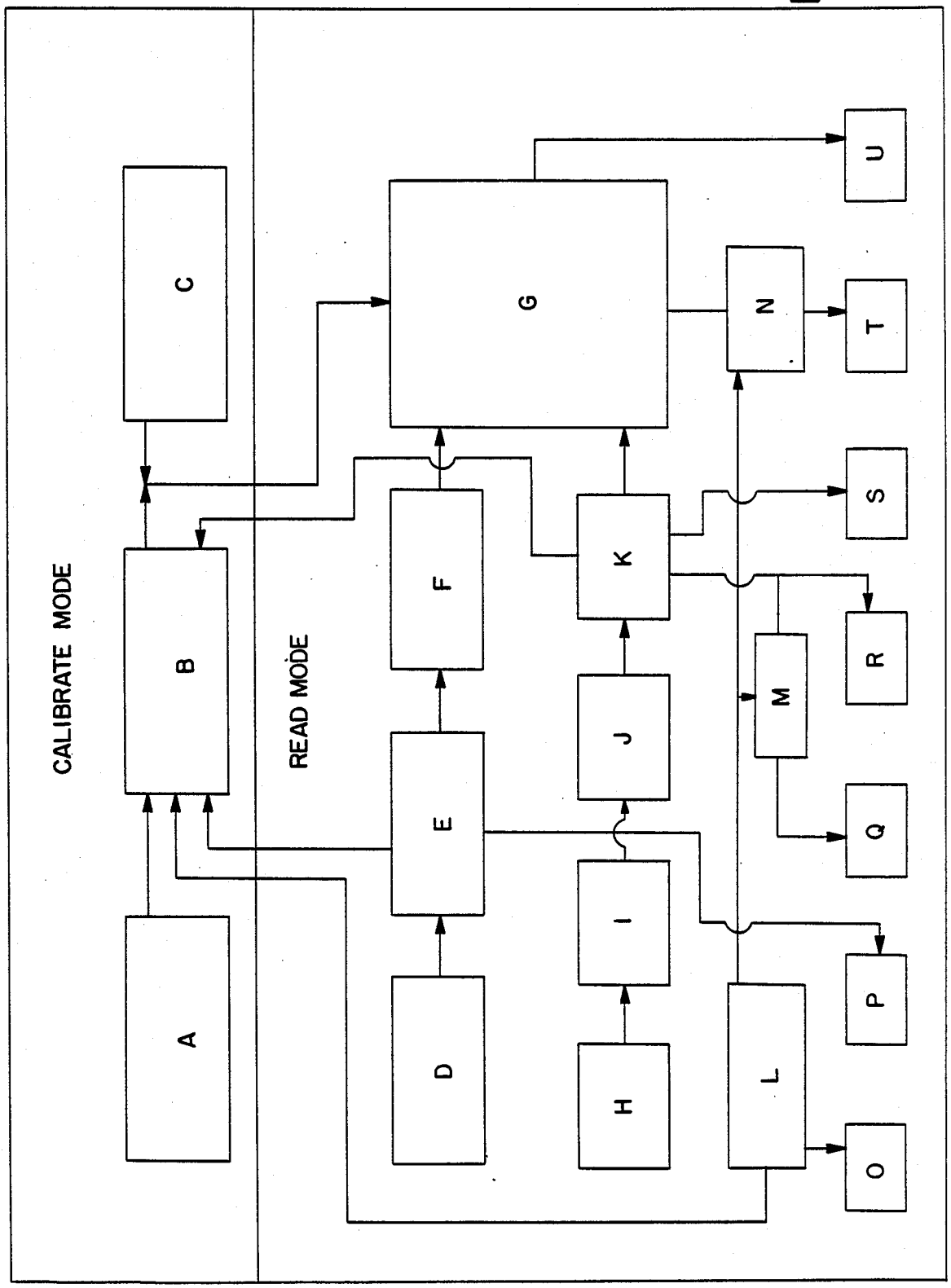
FIG. 2 is a schematic block diagram of the electrical circuit employed by the system of this invention.

In the schematic electrical circuit block diagram of FIG. 2, the following descriptive features are represented by the lettered blocks:

A—Bale Weight (determined by operator and input manually)
B—Determine (Calibration Equations)
C—Predetermined Calibration Equation
D—Pressure transducer
E—Pressure meter
F—Analog to Digital Converter
G—Microprocessor (Calculates instantaneous bale weight using the calibration equation)
H—Resistance sensor
I—Ohmeter (0-20 megaohns)
J—Analog to Digital Converter
K—Calculate % $H_2O$ (10-30%)
L—Magnetic switch activated by bale tie mechanism
M—Calculate bale average % $H_2O$
N—Calculate bale weight
O—Readout bale count
P—Readout Continuous Ram PSI
Q—Readout Bale Average % $H_2O$
R—Readout Instantaneous % $H_2O$
S—Output signal to control water flow rate to hay
T—Readout bale weight
U—Output signal to control pressure on ram While particular examples of the present invention have been shown and described, it is apparent that changes and modifications may be made therein without departing from the invention in its broadest aspects. The aim of the appended claims, therefore, is to cover all such changes and modifications as fall within the true spirit and scope of the invention.

Having thus described my invention, what is claimed is:

1. A bale weight control system for a conventional baling machine having a driver's compartment and a compression zone defined by opposed parallel flat retaining walls capable of being urged together by hydraulic force means, said control system comprising:
    (a) a moisture sensing system which continuously monitors the moisture content of hay passing through said compression zone, and produces an output electrical signal related to the moisture content of the hay being baled,
    (b) a hydraulic pressure sensing system which continuously monitors the hydraulic pressure of said hydraulic force means, and produces an output electrical signal related to said pressure,
    (c) a battery-operated microprocessor adapted to combine the signals from said moisture sensing system and hydraulic pressure sensing system to produce a third output electrical signal related to the weight of a bale being produced at a given point in time, said microprocessor using a definite relationship between moisture content of the hay and hydraulic pressure to determine the bale weight, said relationship being determined by calibration of the system for a given baler, and dependent upon the type of crop being baled,
    (d) electrically controlled valve means responsive to said third signal for adjusting hydraulic pressure and thereby maintaining a constant weight of the bales being produced,
    (e) gauge means activated by said output electrical signals, for providing a continuous indication of the weight of bales being produced as well as instantaneous readings of hay moisture content and hydraulic pressure,
    (f) means for applying controlled quantities of water to the hay,
    (g) electrically controlled valve means responsive to the output signal of the moisture sensing system to adjust the quantity of water applied to the bale in cases where the hay being baled is too dry, and
    (h) electrical conductors which interconnect the moisture sensing system, the hydraulic pressure sensing system, both valve means, the microprocessor and the gauge means.

2. The control system of claim 1 wherein analog-to-digital converters act upon the several output signals.

3. The control system of claim 2 wherein said analog-to-digital converters are located within said driver's compartment.

4. The control system of claim 1 wherein said moisture sensing system utilizes a conductivity meter installed upon one of said walls.

5. The control system of claim 4 wherein said conductivity meter has positive and negative imput terminals.

6. The control system of claim 1 wherein said gauges are located in the driver's compartment.

7. The control system of claim 1 wherein said means for applying water applies said water in the form of steam.

8. The control system of claim 1 wherein said means for applying water may be operated manually or automatically.

* * * * *